US00PP25952P3

(12) United States Plant Patent
Swartz et al.

(10) Patent No.: US PP25,952 P3
(45) Date of Patent: Sep. 29, 2015

(54) RASPBERRY PLANT NAMED 'AUTUMN GLORY'

(50) Latin Name: ***Rubus ideaus* L.**
Varietal Denomination: Autumn Glory

(71) Applicant: FIVE ACES BREEDING LLC, Oakland, MD (US)

(72) Inventors: Harry Jan Swartz, Oakland, MD (US); Eva McCarthy, Faversham Kent (GB)

(73) Assignee: Five Aces Breeding LLC, Oakland, MD (US)

( * ) Notice: Subject to any disclaimer, the term of this patent is extended or adjusted under 35 U.S.C. 154(b) by 0 days.

(21) Appl. No.: 13/998,929

(22) Filed: Dec. 24, 2013

(65) Prior Publication Data

US 2015/0181784 P1 Jun. 25, 2015

(30) Foreign Application Priority Data

Mar. 18, 2013 (QZ) ..... PBR 2013/0883

(51) Int. Cl.
*A01H 5/00* (2006.01)

(52) U.S. Cl.
USPC ..... Plt./204

(58) Field of Classification Search
USPC ..... Plt./204
See application file for complete search history.

*Primary Examiner* — Annette Para
(74) *Attorney, Agent, or Firm* — Rosenberg, Klein & Lee

(57) ABSTRACT

The present invention is a new and distinct primocane fruiting red raspberry cultivar named 'Autumn Glory', which is capable of producing consistent sized, attractive, flavorful and firm fruit that has exceptional consumer appeal characteristics. The cultivar is characterized by its flower truss pattern at the apex of its primocanes, its fruit glossiness and color, and several morphological characteristics including: thorn shape and pattern, leaf vein and margin characteristics, and its compact plant size and fruiting seasons.

8 Drawing Sheets

PRIORITY CLAIM

Figure 1:
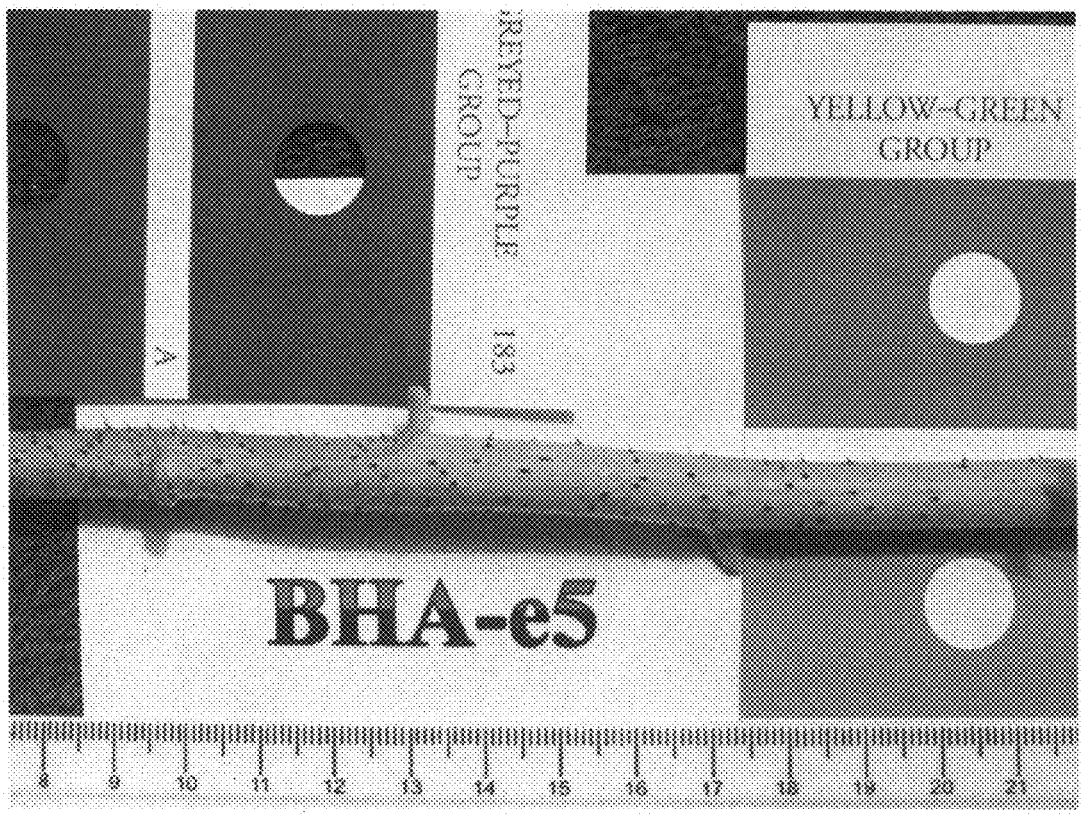

This invention claims priority under 35 U.S.C. §119(f) of application number 2013/0883 filed on 18 Mar. 2013 at the European Community Plant Variety Office (CPVO).

FIELD OF THE INVENTION

This invention concerns a new and distinct cultivar of primocane fruiting raspberry plant with a botanical name of *Rubus ideaus* L. The new cultivar is distinguished from other cultivars by its combination of fruit firmness, balanced flavor, attractive gloss and consistent size and plant growth habit, productivity, relative compactness and long season. 'Autumn Glory' is thereby suitable for premium fresh fruit marketing in commercial production areas worldwide.

DESCRIPTION OF RELATED PRIOR ART

Several cultivars of primocane fruiting (commonly known as "fall bearing") raspberry plants are known. For instance, fall bearing raspberry cultivars named 'Anne', 'Caroline', 'Josephine', 'Driscoll Maravilla', 'Jaclyn', 'Marcela', 'Joan Irene' and 'Marcianna' have been described in U.S. Plant Pat. Nos. 10,411, 10,412, 12,173, 14,804, 15,647, 17,819, 17,986 and 21,007, respectively. The new and distinct cultivar of the present invention is a raspberry plant named 'Autumn Glory'. This new and distinct cultivar differs from 'Anne' in bearing red fruit, while 'Anne' bears golden fruit. Compared with 'Anne', 'Autumn Glory' has significantly higher fruit firmness and primocane yield, but lower floricane yield. 'Autumn Glory' can be distinguished from 'Caroline' in that 'Autumn Glory' fruit is firmer and lighter colored. 'Autumn Glory' plants produce a lower number of canes than 'Caroline' and yield per plant is therefore lower than 'Caroline'. 'Autumn Glory' leaves do not regularly curl in high sun and warm temperatures as 'Caroline'. 'Autumn Glory', like 'Caroline', 'Polka' (unpatented) and 'Marcela', does not produce a commercial floricane, or overwintered, crop of similar size to the primocane crop. 'Caroline' produces smaller sized fruit on floricanes; however, 'Marcela', 'Polka' and 'Autumn Glory' produce quality fruit, but an insufficient proportion of the floricane remains alive after the primocane crop is harvested. Thus, floricane yields are relatively small and produced low on the trellis, making harvest difficult. 'Autumn Glory' can be distinguished from 'Josephine' in that 'Autumn Glory' fruit is produced on primocanes 24 days before 'Josephine' and 'Autumn Glory' fruit is less pubescent and lighter colored when fully ripe. 'Autumn Glory' plants fruit much earlier on primocanes than 'Driscoll Maravilla', resulting in a shorter stature plant. 'Autumn Glory' fruit is glossy, similar to 'Driscoll Maravilla'. 'Autumn Glory' can be distinguished from 'Jaclyn' in that the 'Autumn Glory' fruit is less conic, much firmer, sweeter, much lighter colored and easier to remove from the plant. Both 'Autumn Glory' and 'Jaclyn' ripen very early in the primocane season, produce a second primocane crop later in the fall if the growing season extends into October and November, and the fruit from both cultivars become more difficult to remove in cold weather. 'Autumn Glory' can be distinguished from 'Polka' (unpatented) in having lighter colored, glossier, fruit of similar firmness. 'Autumn Glory' fruit is sweeter than 'Polka'. 'Autumn Glory' primocanes are productive like 'Polka', as both produce multiple or branched peducles or trusses from primocane nodes. 'Autumn Glory' can be distinguished from 'Marcela' in that 'Autumn Glory' fruit is more cohesive and flavorful and less course, due to smaller more uniform drupelets. 'Autumn Glory' plants are also less thorny than 'Marcela'. 'Autumn Glory' differs from 'Joan Irene' in that 'Autumn Glory' fruit are glossier, lighter colored and firmer than 'Joan Irene'. 'Autumn Glory' produces a primocane crop several weeks earlier than 'Joan Irene'.

ORIGIN OF THE NEW CULTIVAR

The new cultivar of fall bearing red raspberry originated from a controlled cross by Five Aces Breeding LLC of Oakland, Md. at rented glasshouse facilities in College Park, Md. The cross, designated: "HA", was XAT-k4 (unpatented)× 'Polka' (unpatented) and was made in the winter of 2007. XAT-k4 is a very early season primocane fruiting red raspberry selection with several interesting fruit quality attributes, including flavor, fruit size, deep red-purple color and reasonable fruit firmness. 'Polka' also is an early season primocane fruiting cultivar with several desirable fruit attributes, such as firmness and lighter color. The cross was made to produce a very early primocane type to advance the current fall season to overlap the late spring season cultivars.

XAT-k4 is a cross of 'Jaclyn' (U.S. Plant Pat. No. 15,647)× PBP-b2. 'Jaclyn' is a cross of OBC-f1 (unpatented)×'Caroline' (U.S. Plant Pat. No. 10,412). OBC-f1 is a selection from the cross KP-2×KAS-1. KP-2 (unpatented) is from a cross of CFO-1×GEN-1. CFO-1 (unpatented) is a cross of 'Southland' (unpatented)×'Willamette' (unpatented). GEN-1 (unpatented) is a cross of an F2 of *R. pileatus*×SCRI 8216B6 (unpatented). KAS-1 (unpatented) is a cross of GDF-3 (unpatented)×*R. stellarcticus* 'Linda' (unpatented). GDF-3 is a cross of selection SCRI 52B6 black-purple raspberry (unpatented)×'Autumn Bliss' (U.S. Plant Pat. No. 6,597). PBP-b2 is a cross of 'Josephine' (U.S. Plant Pat. No. 12,173)×DCB-4, selected in 1999 in Blackstone, Va. 'Josephine' is a cross of 'Amity' (unpatented)×'Glen Garry' (unpatented) selected in Cream Ridge, N.J. DCB-4 is a cross of 'Southland' (unpatented)×AmosH (unpatented), selected in 1984 at the Wye Institute of the University of Maryland on the eastern shore of Maryland.

SCRI designated selections are by courtesy of the Scottish Crop Research Institute, Invergowrie, Scotland, United Kingdom (via. Dr. Derek Jennings). The other selections are from the University of Maryland at College Park; Rutgers University of New Brunswick, N.J.; Virginia Polytechnic Institute and State University, Southern Piedmont Agricultural Research and Education Center at Blackstone; and the University of Wisconsin at River Falls cooperative breeding program.

The year of crossing was designated "B" as part of the Five Aces Breeding Certified Raspberry Breeding Program. The seed from this cross was exported to the United Kingdom, germinated and grown to transplant size by Edward Vinson Ltd. at their Kemsdale Farm, Faversham, Kent United Kingdom. The seedlings were transported to Cartaya, Spain and planted in the field under tunnel in April, 2008. The present invention was fifth seedling of the "BHA" progeny selected in November 2008 and was therefore designated "-e5". Thus, the complete breeding designation of 'Autumn Glory' is "BHA-e5". The synonym for "BHA-e5" in Europe is 'Jade'.

SUMMARY OF THE NEW CULTIVAR

This application relates to a new and distinct red fruited, primocane fruiting, raspberry cultivar, botanically known as *Rubus ideaus* L. The following characteristics are outstanding:

1. Production of an extended season of fruit on primocanes with a primary early crop at the apex of the cane followed by an extended crop on later arising canes and, if the season is sufficiently long, from lateral buds subtending the nodal positions which bore the primary primocane crop. These later primocane fruit are usually larger sized and firmer than earlier fruit produced at higher temperatures.
2. Compared to these extended season primocane cultivars, 'Autumn Glory' is very attractive, being a favorable combination of fruit glossiness, bright, light red color and uniformity and small size of drupelets.
3. 'Autumn Glory' canes are more productive than other compact sized plant primocane fruiting selections tested, having large numbers of fruit per fruiting node. These high numbers are obtained by multiple peducles, branched peducles or branch trusses per node, each arising from the axillary region between the leaf petiole and cane.

These characteristics make 'Autumn Glory' suitable as a summer and fall primocane fruiting type for premium fresh fruit marketing in commercial production areas worldwide. In cooler areas with less than 2500 growing degree days (base 50° F.), 'Autumn Glory' primocane fruit ripens in the last week of July or early August and through September, making it sufficiently early to use as a primocane bearer for almost all agricultural regions in the United States. In areas with an extended growing season, a second flush of fruit will be produced from primocane nodes below the primary fruiting nodes or from new later forming canes from the ground.

The following characteristics are useful in distinguishing this cultivar from other cultivars and can be useful for cultivar identification. Plants used for these observations were grown in uncrowded conditions in clear plastic unshaded tunnels or greenhouses.

1. When cane density is below 6 canes per meter of row on non-tissue culture propagated plants at least two years old, 'Autumn Glory' plants produce primocanes which terminate in flower clusters. 'Autumn Glory' canes usually produce flowers at the $19^{th}$ node in pots in tunnels at 3000 ft. elevation in Maryland, United States. By comparison, 'Jaclyn', 'Marcianna', 'Caroline' and 'Heritage' (unpatented) produce fruit, on average, at the $15^{th}$, $24^{th}$, $25^{th}$ and $29^{th}$ nodes, respectively. Above the $19^{th}$ node, an additional 11 nodes produce flower trusses during the first flush of fruit and an additional 3 nodes produce flowers during a second flush of growth after the primary crop has ripened; therefore, 42% of an average, well illuminated, 'Autumn Glory' primocane produces flowers. The second flush of primocane crop comes from several buds immediately subtending the most basal primocane fruiting truss or node. This second flush begins over a month after the primary primocane crop has finished and fruit from this truss is larger than normal primocane or floricane fruit.

2. 'Autumn Glory' fruit is light colored and glossy in appearance. Fruit can be picked at The 1995 Royal Horticultural Society Color Plate No. 44B in summer. Fruit ripens to Royal Horticultural Society Color Plate 45A, then darkens to Plate 59A or 59B at overripe. In contrast, 'Marcianna' fruit, considered also to be light colored, is pickable at the darker 1995 Royal Horticultural Society Color Plate No. 46B.

3. Several morphological traits are distinctive in 'Autumn Glory'. Thorn (spine, bristles or prickles) color pattern, size and number per node vary by genotype, but are consistent over most environments. 'Autumn Glory' thorns are always very numerous especially at the base of the cane as typical of the species. The dark red color, extension of the color into the cane and long shape are consistent in the clone. Thorn coloration is consistently deep grayed purple (1995 Royal Horticultural Society Color Plate No.183A) and the coloration extends about 1 mm. in an oval into the surrounding cane. Thorns are generally 2 mm. in length, relatively thin and slightly downward pointed. These needle like thorns lose their red color, turning a light brown (1995 Royal Horticultural Society Color Plate No. 177D) at their tip in summer. This change continues throughout the thorn by the end of the fall season.

4. Leaf veins are light green (1995 Royal Horticultural Society Color Plate No. 144B) similar to the color of the petioles and petiolules. The veins are particularly prominent on the underside of the leaf, with over 80% of the circumference of the major veins not buried in the leaf lamina.

5. The margins of the leaves are simple saw-toothed, less compound that other cultivars. The margins of the sepals have narrow pubescence stripes at their margins. The stipules are fused to the petiole for half their length.

6. The primocane apical flower truss extends to lower nodes, as is typical of early fruiting fall bearing cultivars. Unlike those cultivars, 'Autumn Glory' has shorter lateral trusses at the apical nodes and large leaves at the same nodes. This combination of traits results in fruit hidden by leaves, especially in the top portion of the primocane truss.

BRIEF DESCRIPTION OF THE PHOTOGRAPHS

Figure 5:
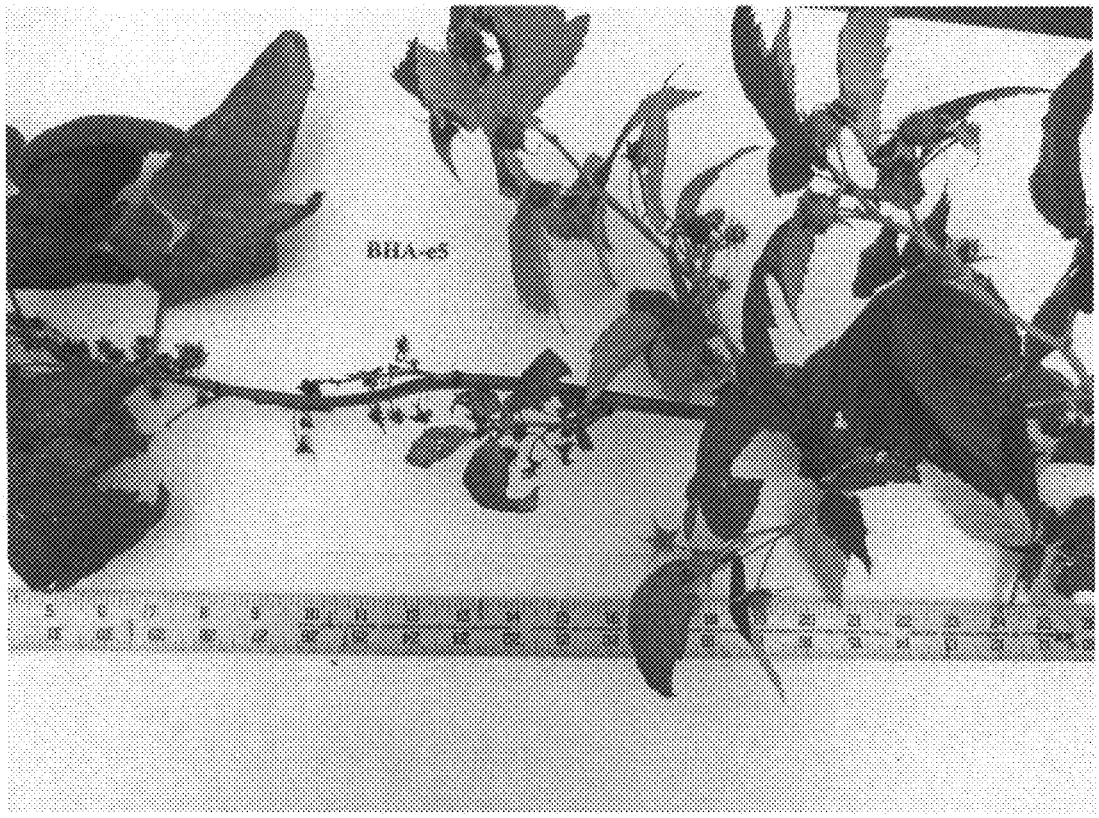

The accompanying photographs show typical characteristics of the new variety, the measuring stick is in numbered centimeters in FIGS. 1, 2, 2A, 3, 3A and 6 and in inches in FIG. 5:

FIG. 1. shows a 'Autumn Glory' primocane section with The 1995 Royal Horticultural Society Color Plates Nos. 144B for the cane color and No. 183A for the thorn color.

Figure 2:
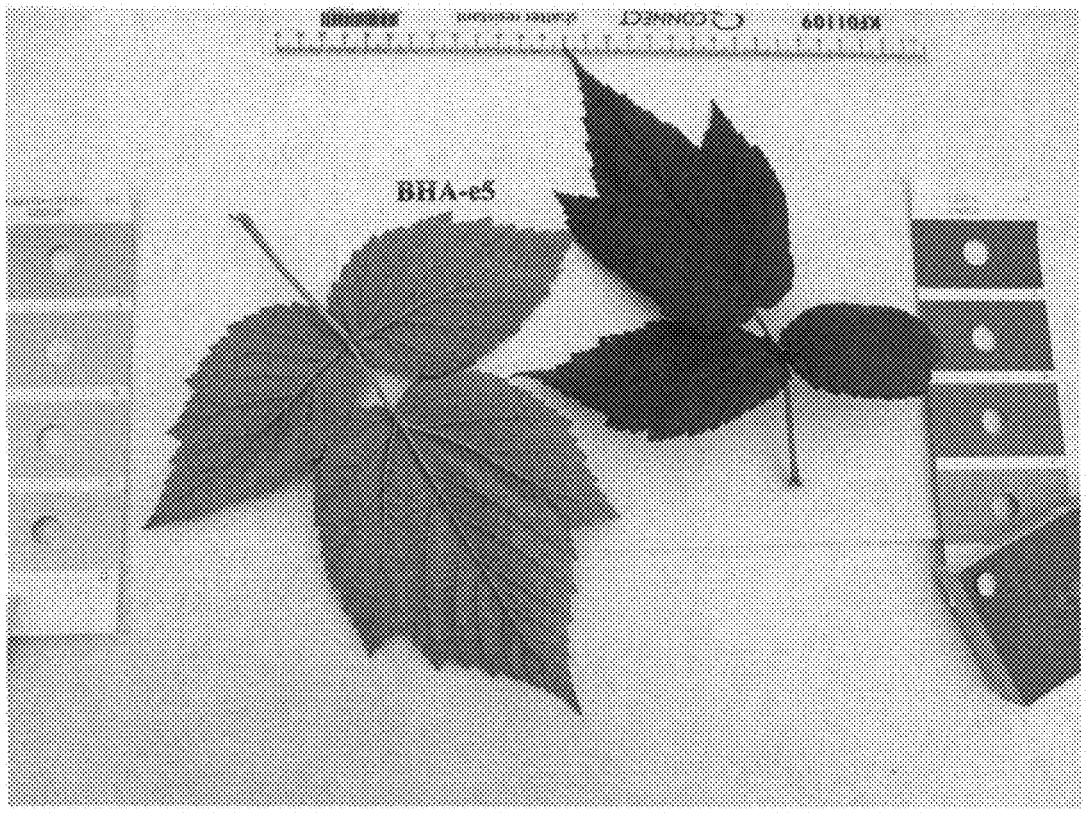

FIG. 2. shows both sides of trifoliolate 'Autumn Glory' leaves and their leaf size margin serration and vein pattern and Royal Horticultural Society Color Plates Nos. 143 A and 193A.

Figure 2A:
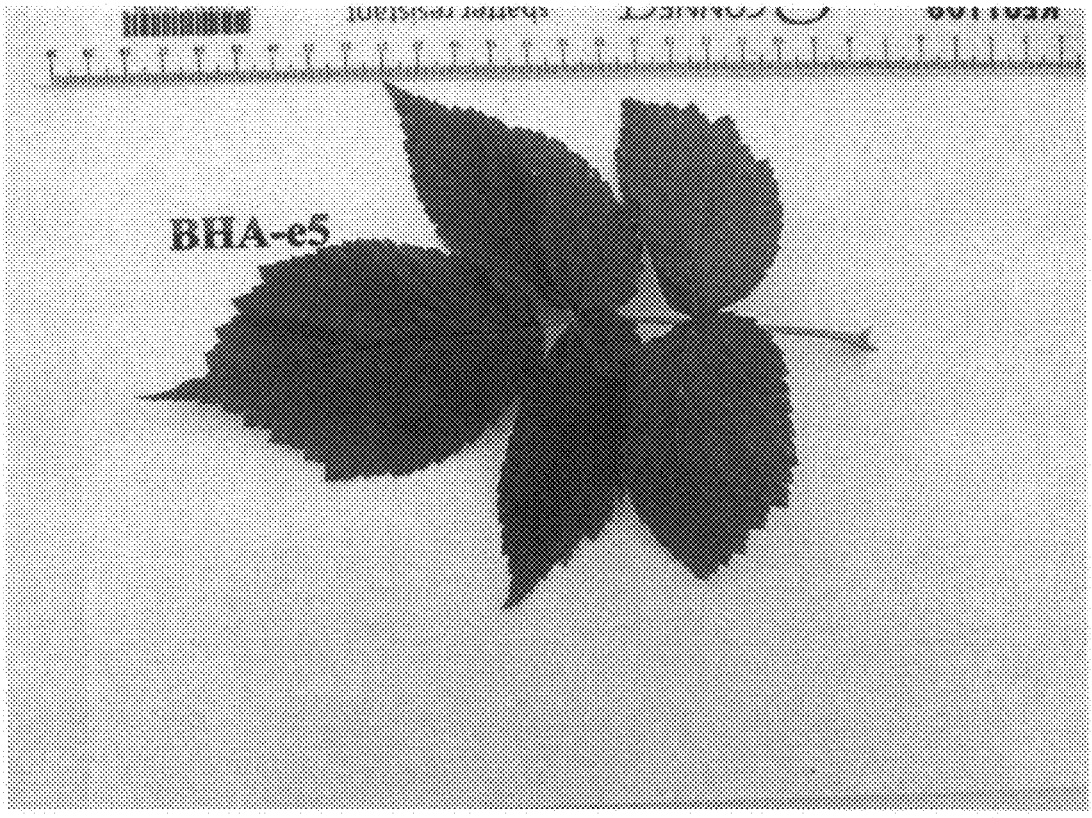

FIG. 2A shows the upper surface of a pentafoliolate 'Autumn Glory' leaf and its leaf size margin serration and vein pattern.

Figure 3:
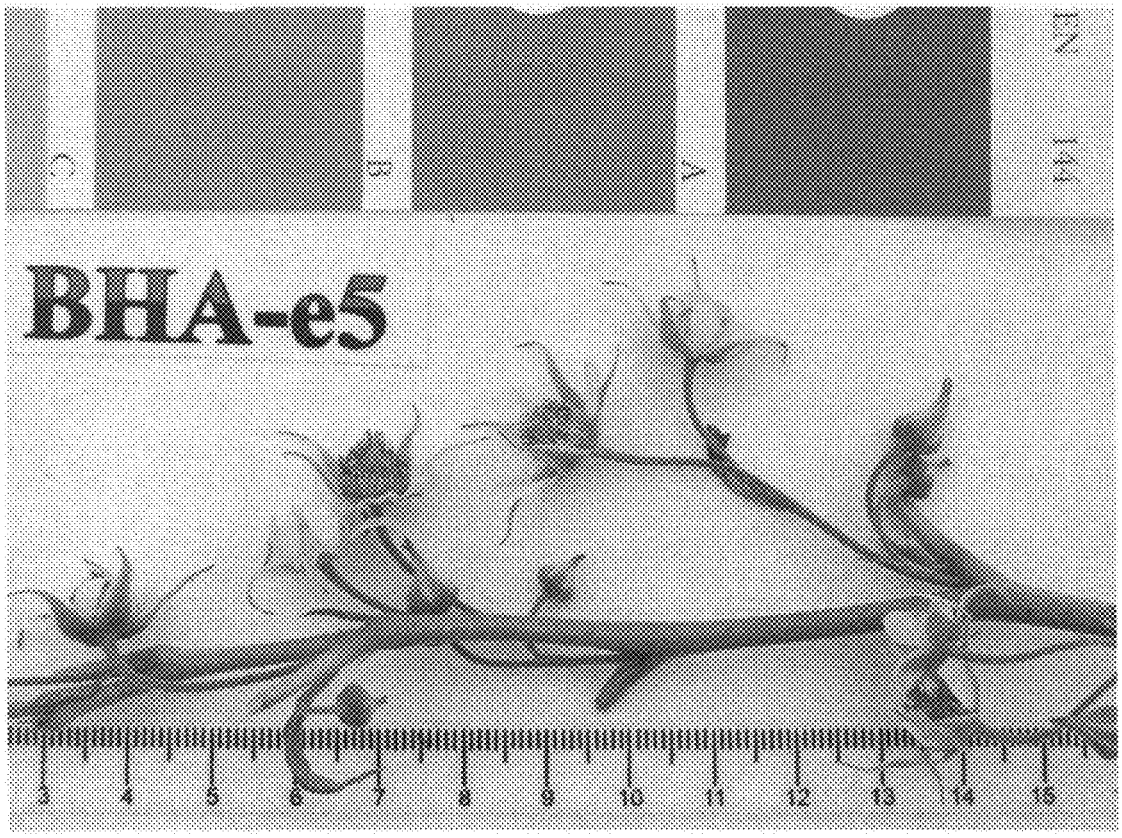

FIG. 3. Shows 'Autumn Glory' flowers and short apical primocane trusses, or fruit arising directly from the leaf axil with The 1995 Royal Horticultural Society Color Plate No. 144 for cane and peduncle color comparison.

Figure 3A:
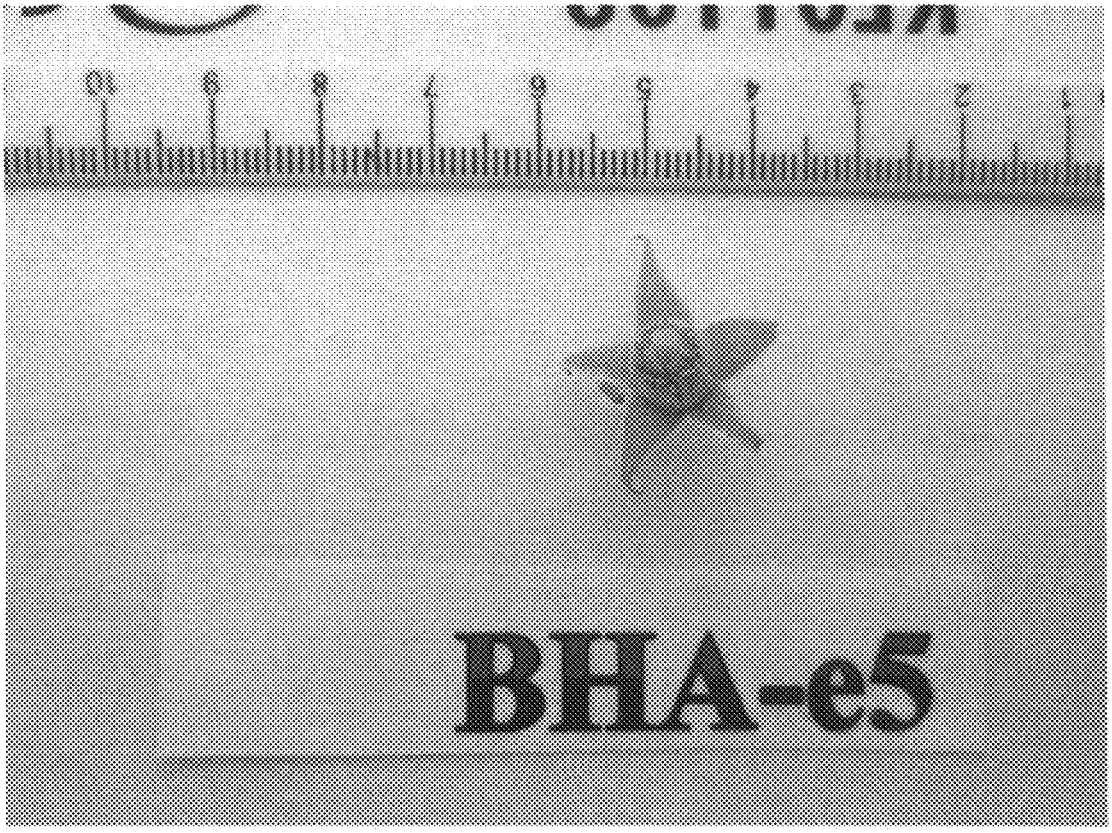

FIG. 3A. shows an 'Autumn Glory' flower.

Figure 4:
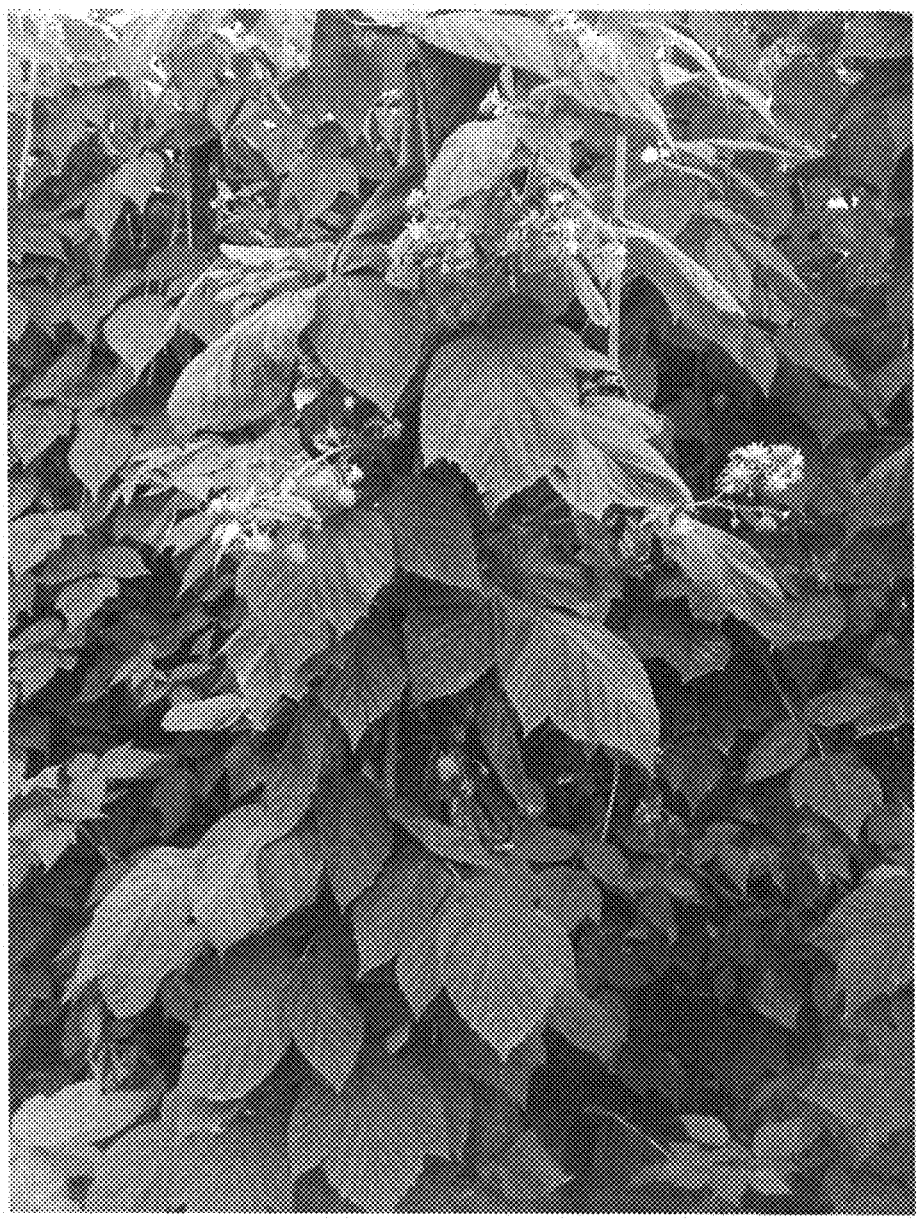

FIG. 4. shows a primocane fruiting cluster of 'Autumn Glory', showing the exposure of 'Autumn Glory' fruit as grown in an unheated tunnel. Note the overgrowth of leaves at the apex of the cluster hides the fruit.

FIG. 5. shows the secondary flush of lateral fruit trusses on an 'Autumn Glory' primocane. The location is, on average, at the $9^{th}$ through $12^{th}$ nodes basal to the apex.

Figure 6:
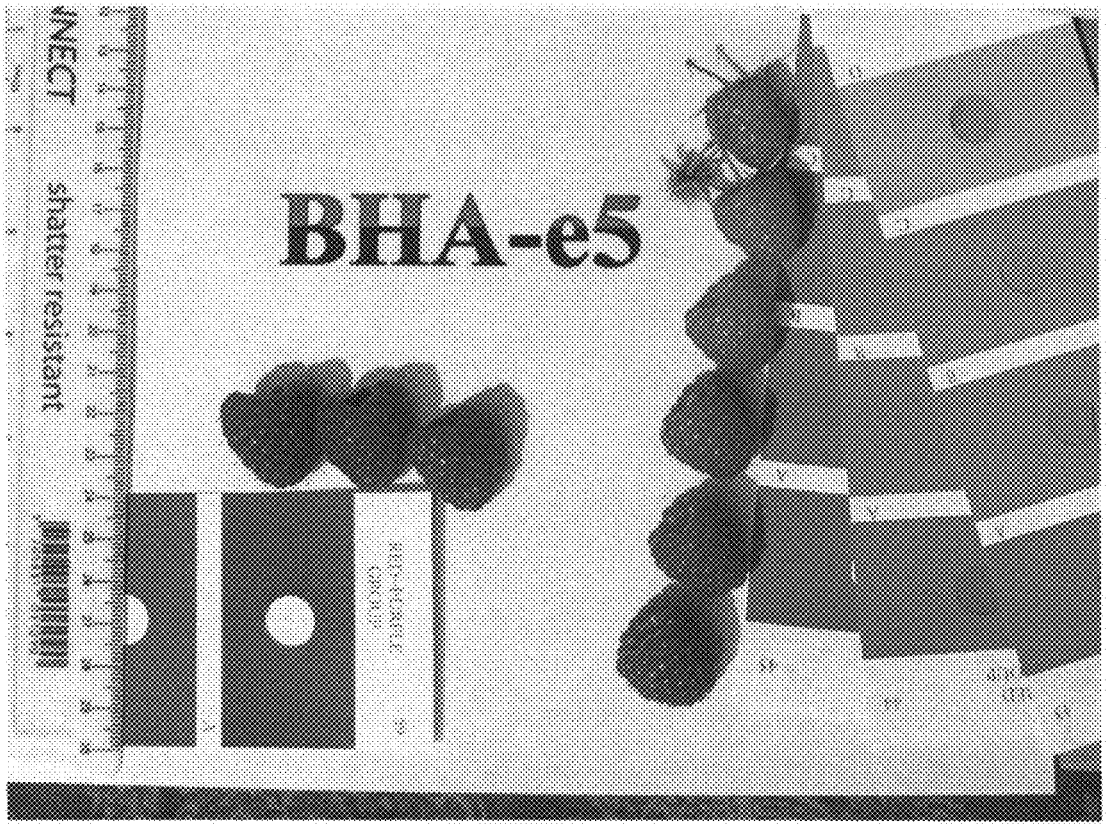

FIG. 6. shows the lighter color of 'Autumn Glory' fruit and The 1995 Royal Horticultural Society Color Plate Nos. 43, 44 and 45, and the darker overripe fruit near The 1995 Royal Horticultural Society Color Plate No. 59. The six fruit on the right are arranged by stages of ripeness, the ripest being at the bottom. The top two fruit are the only ones not easily removed from the receptacle.

DESCRIPTION OF THE NEW CULTIVAR

The following is a detailed description of 'Autumn Glory', the new cultivar, including fruit production, together with the cultivar's morphological characteristics. 'Autumn Glory' is a species hybrid, which contains a predominance of *Rubus ideaus* L. traits and would be botanically classified in that species commonly referred to as red raspberries. The description is based on information provided by cooperating growers from plants grown in tunneled fields at Faversham, Kent, England and Cartaya, Spain and from plants grown in the greenhouses at Oakland, Md. As these climates differ, particularly in temperatures experienced in the growing season, we believe the description of 'Autumn Glory' will be consistent in other locations.

'Autumn Glory' produces a moderate number of root- and crown-suckers (approximately 13 per 10 gallon pot with a one year old plant in April), more than 'Anne' and 'Josephine', similar to 'Marcianna', but less than 'Caroline' and 'Heritage' (unpatented). Young plants can produce more canes after the first flush, especially when the initial canes are removed or damaged. During the growing season, canes are light green colored (1995 Royal Horticultural Society Color Plate No. 144B) (FIG. 1) with a red blush (1995 Royal Horticultural Society plate No. 184A) on only very well lighted portions of the cane. Canes have a very light pubescence and are usually unbranched when vegetative and semi-erect by the second year of a plant's growth. Total node number per cane is 33 for second year adult, non-tissue culture plants. By comparison, 'Heritage' produces 39 nodes per cane, 'Caroline' produces 36 nodes per cane on tissue culture produced first year plants, 'Marcianna' produces 40 nodes per cane and 'Josephine' produces 45 to 48 nodes per cane. Vegetative growth is moderately vigorous, being terminated by floral development, reaching on average 4 feet in full sun, or 6 feet in crowded conditions or in tunnels. Internode length at 30 cm. above ground in well lighted plants without floricanes is 3.72 cm. Cane diameter at the same location was 1.0 cm. Canes develop their normal woody color in the fall changing from green to the red blush color then to dark brown with approximately on quarter of the cane area having lighter patches (1995 Royal Horticultural Society Color Plate No. 177B to 177 D). 'Autumn Glory' dormant canes only slightly exfoliate.

Thorns are many in density; ranging from 70 to 172 per internode, with an average of 112 at 30 cm. cane height and an average of 27.4, and range of 14-56 per internode at the apex of the cane. Thorn shape is straight and needle-like, (the length of the thorn is greater than ten times its diameter) and slightly downward pointing; full sized thorn length is approximately 2 mm. (FIG. 1). 'Autumn Glory' thorn color is mostly grayed purple (1995 Royal Horticultural Society Color Plate No. 183A) in color; including 1 mm. of the surrounding epidermis of the cane This thorn coloration of the cane is in an oval oriented with the long axis parallel to the axis of the cane. By the last months of the growing season, the tip of the thorn becomes brown (1995 Royal Horticultural Society Color Plate No. 177D). The color of the thorns turns completely brown (1995 Royal Horticultural Society Color Plate No. 177D in the dormant season, matching that of the overwintering floricanes. A similar pattern occurs with lateral buds, which turn green to brown (1995 Royal Horticultural Society Color Plate No. 177A) and are typical in size and shape of the species. No secondary buds were observed on 'Autumn Glory'.

The lower surface of primocane 'Autumn Glory' leaves is pubescent grey-green resembling the 1995 Royal Horticultural Society Color Plate No. 193A (FIG. 2). The upper surfaces of both primocane leaves are medium green, most closely in hue to the 1995 Royal Horticultural Society Color Plate No. 143A, depending on the amount of N fertilization and time of season (FIG. 2). Senescing leaves have a green yellow color resembling the 1995 Royal Horticultural Society Color Plate No. 146A. Leaves abscise readily in October and November.

Vigorous plants have leaves that are 90% trifoliolate and 10% pentafoliolate at nodes 1 to 18. Above this, only trifoliolate leaves occur. The pentafoliolate terminal leaflet is, on average, 6.6 cm. wide and 11.0 cm. long (FIG. 2A). The trifoliolate terminal leaflet is, on average, 9.6 cm. wide and 14.0 cm. long. The pentafoliolate maximum leaf width, measured from apex of a lateral leaflet to the opposite lateral leaflet apex is, on average, 16.9 cm. The trifoliolate maximum leaf width, measured from apex of the lateral leaflet to the opposite lateral leaflet apex is, on average, 22.9 cm. The width of the basal lateral leaflet for pentifoliolate and trifoliolate leaves averaged 5.4 cm and 6.6 cm, respectively. The pentafoliolate leaf petiole, basal petiolule and apical petiolule lengths averages 6.8 cm, 3.3 cm and 1.2 cm, respectively, for a total of 11.3 cm. The trifoliolate leaf petiole and terminal petiolule lengths averaged 7.1 cm and 3.4 cm, respectively. Petioles, petiolules and leaf veins have a similar color to the midseason primocane (1995 Royal Horticultural Society Color Plate No. 144B). Petioles average 26.0 reduced size thorns, with very reduced thorns occurring on the leaf midrib. Lateral leaflets are sessile and join at the petiole apex with the apical leaf petiolule (FIG. 2). Leaf serration is relatively simple sawtooth. Leaves have moderate laminar puckering and veination pattern are common for most cultivars of red raspberry and cannot be used to distinguish this cultivar. Leaf veins are very pronounced on the undersurface of the leaf, with less than 20% of the circumference buried in the leaf lamina. Leaf stipules are bladelike and 0.8 cm in length in total; the basal one half of their length is fused to the petiole sides creating a very slightly flanged petiole typical of *Rosa* species.

Flowers appear after 21.6 nodes, on average, on adult plant 'Autumn Glory' primocanes. By comparison, adult 'Marcianna', 'Heritage' and 'Josephine' primocanes flower, on average, after 23.8, 28.5 and 35.8 nodes respectively. Fruit appears on 10.7 nodes on average. If the growing season is sufficient, and average of 3.0 additional buds subtending the floral area will break and produce flowers. When this occurs, fruit is borne on 42% of the total nodes of the primocanes. The proportion of cane producing fruit is greater than 'Heritage' (27%), 'Caroline' (29%), 'Josephine' (21%) or 'Marcianna' (42%) and, by observation in other fields, this proportion in 'Autumn Glory' is also greater than that of 'Anne', 'Autumn Bliss' (U.S. Plant Pat. No. 6,597), 'Autumn Britton' (unpatented), 'Amity' (unpatented) or 'Ruby' (U.S. Plant Pat. No. 7,067). 'Autumn Glory' primocanes will have delayed flowering if overfertilized or grown in shaded conditions, such as occurs when spacing between rows is less than 1 meter.

The unscented flower morphology and early fruit morphology is typical of most red raspberry cultivars, having five white (1995 Royal Horticultural Society Color Plate No. 155D) petals that average 0.7 cm. long, 0.4 cm. wide (FIG. 3A); petals abscise after pollination. Flowers have five 0.9 to 1.3 cm. long, 0.40 to 0.5 cm. wide at the base triangular grey green sepals (1995 Royal Horticultural Society Color Plate No. 191B) on green peduncles (1995 Royal Horticultural Society Color Plate No. 144B) (FIG. 3). The internal sepals have two stripes of pubescence running along their outside length, as typical of red raspberries. 'Autumn Glory' sepal stripes are thinner than several cultivars. Sepals are longer on primary fruits and will occasionally have a slight red blush. Mid season floricane flowers have on average 40.4 pistils on midseason fruit and a similar number of anthers, 45.2; primocane flowers have 61.6 pistils and 62.9 anthers. Anther and pistil color is similar to the 1995 Royal Horticultral Society Color Plate No. 157A; none of these traits can be used to identify 'Autumn Glory'. Floricane peducle length is 1.5 cm. with a color similar to the cane and petioles of leaves, 1995 Royal Horticultural Society Color Plate No. 144B. Primocane fruit peducle length averages 2.4 cm. with the same color and 11.2 minute thorns on average.

Floricane flower trusses are typical cymose clusters; with 8 nodes bearing flowers apical to on average 5 nodes without flowers. Floricane trusses produce on average 20.1 flowers and are 9.2 inches in length.

Primocane flower truss morphology is unusual, and represents a key identifying feature of 'Autumn Glory'. The floral zone of the primocane results from the terminal apex flowering and subtending lateral buds producing floral clusters. The inflorescence is a compound cyme, with lateral trusses arising from axillary buds on the cane. Apical flowers are first to open on laterals and on the main cane. In 'Autumn Glory', the apical 6 lateral buds produce very short trusses and multiple fruit from unbranched or branched peduncles (FIG. 3). More basal buds produce elongated trusses with trifoliolate and monofoliolate leaves (FIG. 4). The average lateral truss length in cm. and number of flowers (in parentheses), arising from an axillary bud position, from the apex is: 2 (4), 1 (3), 2 (4), 2 (4), 2 (4), 2 (6), 3 (4), 3(8), 8(10), 8(10), 11 (12), 9 (8), 8(9). Thus, the laterals arising from the apical 7 lateral nodes, on average, produce 4.5 fruit per node on short 1.97 cm long (average) laterals with branched and unbranched peducles arising from the short lateral or the axillary bud directly. Primocane leaves obscure these fruit readily, this trait is typical of one of the great grandparents, AmosH (unpatented). Flowering also occurs from the $8^{th}$ to $12^{th}$ nodal position from the apex. The laterals from these positions on average produce 9.8 fruit and are 8.9 cm in length. Fruit from these positions can be seen more readily emerging from the primocane leaf canopy. On average, 80.3 fruit are produced on the initial flush of primocane flowering. If the season is sufficiently long (until October), a secondary flush of axillary truss development occurs on approximately half of the nodes 13 to 16 on well-developed canes (FIG. 5). These nodes produce 8.53 fruit per node borne on 11.2 cm long lateral trusses 93 days later, when measured midseason, than the initial primocane fruit. The season gap between the end of the primary flush and the beginning of this secondary flush is 39 days. This behavior is also seen in the variety 'Jaclyn', one of the grandparents of 'Autumn Glory'. On average, an additional 25.6 fruit are produced per cane on this secondary flush. Additional late fruit is borne on later arising primocanes, which progress through the normal primary primocane pattern of flowering and fruiting.

'Autumn Glory' fruit size and weight are moderate, but relatively consistent through the season. Early primocane averaged 2.2 cm long and 2.0 cm wide with a cavity of 0.86 cm in diameter. Later primocane fruit averaged 2.1 cm in length, 1.9 cm wide with a cavity of 0.82 cm in diameter. Floricane fruit was similar in size, 1.9 cm in length, 2.0 cm in width and a cavity of 0.88 cm. in diameter. Fruit weight was 2.4 grams from the floricane crop and 2.6 grams from the primary primocane crop. These results were obtained in potted plants, in field trials in the United Kingdom, average fruit size for the primocane crop was 6.09 grams. The secondary primocane crop or primary crop from later primocanes averaged 3.4 grams. The fruit width to receptacle cavity is 43-44% of the fruit diameter, compared to 30% of the long conic fruited 'Jaclyn' and the round 'Josephine', which has a cavity 40% of the fruit diameter (FIG. 6). The consistent fruit width to length ratio of nearly 1 to 1, is indicative of this spherical fruit. This ratio is smaller than conic-fruited 'Jaclyn', a grandparent of 'Autumn Glory', but similar to 'Josephine', a great grandparent, and 'Polka', a parent, which have more nearly round fruit. The fruit receptacle is not highly globular at its base, causing no distension of the fruit at the midpoint of its longitudinal axis (FIG. 6).

'Autumn Glory' fruit have 83 drupelets for the first 3 primocane harvests with average fruit weight of 3.9 grams; later harvests average 50 drupelets; this is a relatively small variation in fruit size over the season. 'Autumn Glory' fruit are cohesive, unless pollination problems exist, the fruit does not shatter under pressure of hand harvest.

Fruit ripens 35 days after pollination on primocanes in a greenhouse in Oakland, Maryland. In tunnels, potted primocane fruit ripened beginning July 24$^{th}$ and harvest extended to September 12$^{th}$ Under protected culture, fruit again was produced from second flush trusses beginning October 24$^{th}$. Floricane fruit was initially ripe on June 14$^{th}$ and continued until July 9$^{th}$.

'Autumn Glory' primocane fruit are medium red when ripe, closely resembling the hue of The 1995 Royal Horticultural Society Color Plate No. 45A and slightly lighter color when underripe, resembling The 1995 Royal Horticultural Society Color Plate No. 44B (FIG. 6). When fully or over ripe, or upon more than 7 days storage, fruit develops a darker red color, starting at The 1995 Royal Horticultural Society Color Plate No. 59B and finally at No. 59A. Except when temperatures fall into the 50°'s during the day, fruit is pickable at color 44B, but not at 43C, which is too immature to harvest without shattering (FIG. 6), the top two fruit, with peduncles and sepals, are not easily harvestable). Floricane fruit are slightly lighter when ripe, 1995 Royal Horticultural Society Color Plate No. 45A. Fruit have a very slight amount observable pubescence, much less than most other commercial cultivars. Drupelet arrangement is uniform resulting in good fruit cohesion. The combination of light color, symmetry and lack of fuzziness results in consistently excellent "attractiveness" scores. Commercially picked fruit does not break down after at least one week in common storage at 40 F. Flavor is sweet, unlike 'Polka' and other early maturing primocane cultivars, which can be acid in warmer weather. The texture of the fruit is firmer than other eastern US-grown red raspberry cultivars known to us, with the exceptions of 'Josephine', 'Driscoll Maravilla' and 'Polka', all primocane fruiters with similar firmness.

FRUIT PRODUCTION

'Autumn Glory' has been tested in a glasshouse in Oakland, Md. The following data were collected in potted plants in the summer and fall of 2013. In pot, 'Autumn Glory' averaged 225.6 grams per plant from floricanes and 980.8 grams per plant in the primary primocane season and an additional 290.8 grams per plant in the secondary flush. Primary primocane yield per cane is 245.2 grams on plants with 4 canes per pot. At the spacing used in these measurements, the primocane yield was 2.12 kg/meter of row for potted 'Autumn Glory' plants in 0.4 m between plant×1 m between rows spacing in tunnels. Yield in tunnels at this spacing would be 9,498 kg/ha or 8,358 lbs per acre, assuming 4 rows per 30 ft. wide tunnel, half the density at which that the plants were tested. In a United Kingdom field test, 'Autumn Glory' averaged 3.24 kg/meter of row, with a per cane yield of 360 grams. Yield would be 14,516 kg per hectare or 12,774 lbs per acre. This yield is similar to 'Marcianna', but less than 'Caroline', which is too soft for the commercial trade.

The plant is slightly susceptible to late season leaf rust (yellow rust). The plant's reaction to *Phyophthora fragariae* var. *Rubi* root rot is probably moderately resistant, based on field reaction, not on controlled testing. When plants were excessively watered in pots in a glasshouse, symptoms of *Phytophthora fragariae* var. *Rubi* were not observed, while other genotypes succumbed to this root rot and had *Phytophthora* sp. isolated from their infested tissues. Fruit is usually free from *Botrytis* rot in the field, more so than 'Anne' and 'Caroline', but not 'Josephine'

'Autumn Glory' can be asexually propagated by tissue culture or by root suckers. No off-type plants have been observed in the history of asexual propagation of this cultivar by either method.

What is claimed:

1. A new and distinct fall bearing red raspberry plant known as 'Autumn Glory' as described herein, illustrated and identified by the characteristics set forth above.

* * * * *